United States Patent [19]

Mattner et al.

[11] 4,071,557

[45] Jan. 31, 1978

[54] PREPARATION OF 2-SUBSTITUTED AMINOPHENYL KETONES

[75] Inventors: Paul G. Mattner, Brooklyn, N.Y.; Joseph A. Smith, Fanwood, N.J.

[73] Assignee: Sandoz, Inc., E. Hanover, N.J.

[21] Appl. No.: 653,362

[22] Filed: Jan. 29, 1976

[51] Int. Cl.$^2$ ............................................. C07C 97/10
[52] U.S. Cl. .................... 260/570 AB; 260/329 S; 260/329 AM; 260/332.3 R; 260/332.5; 260/340.5 R; 260/347.3; 260/347.7; 260/346.22
[58] Field of Search ............... 260/570 AB, 570.5 C, 260/570.6

[56] References Cited

U.S. PATENT DOCUMENTS 3,253,034  5/1966  McLoughlin ............... 260/570.5 X
3,463,808  8/1969  Bond et al. .................. 260/570.6 X

OTHER PUBLICATIONS

Borch et al., "J.A.C.S.", 93, 12, pp. 2898–2904 (1971).
Gribble et al., "J.A.C.S.", 96, 25, pp. 7812–7814 (1974).
Gribble et al. (II), "Synthesis", pp. 650–652 (1975).
Borch et al. (II), "J.A.C.S.", 91, 14, pp. 3996–3997 (1969).
Borch et al. (III), "J.A.C.S.", 37, 10, pp. 1673–1974 (1972).
Gribble et al. (III) "J. Chem. Soc. Comm.", pp. 535–536 (1975).
Guimenini et al., "Z. Narturforsch", Sect. B 30, pp. 820–821 (1975).
Gaylord, "Reduction With Complex Metal Hydrides", pp. 16, and 32–33 (1956).
Wagner et al., "Synthetic Organic Chemistry", pp. 324–325 (1963).

*Primary Examiner*—Robert V. Hines
*Attorney, Agent, or Firm*—Gerald D. Sharkin; Richard E. Vila

[57] ABSTRACT

Substituted aminophenyl ketones such as 2-alkylaminobenzophenones are prepared by reacting a corresponding 2-aminophenyl ketone with a ketone or aldehyde, a borohydride and strong acid.

23 Claims, No Drawings

PREPARATION OF 2-SUBSTITUTED AMINOPHENYL KETONES

Compounds such as 2-alkylaminobenzophenones are chemical intermediates of great and increasing importance, such as in the preparation of pharmacologically active compounds. The efficient preparation of such phenyl ketones is therefore of corresponding high importance and has been more difficult or costly than might be expected considering the interest in such compounds and their relatively simple structure. A major problem area has been the alkylamino group in terms of how and when it can be best created or introduced in the overall synthesis. One approach has been to merely alkylate the corresponding amino group. However, this approach has presented difficulties in terms of efficiency and the avoidance of substantial by-product formation and other factors influencing yield. For example, the direct alkylating procedures often result in the formation of substantial quantities of a dialkylamino by-product and are not easily controlled in this respect. Such dialkylamino by-product formation can be avoided by procedures involving tosylation, alkylation and detosylation but the two extra steps required in this procedure constitute one of its major drawbacks. A recent development limited to isopropylamino compounds which are of substantial interest in preparation of the anti-inflammatory quinazolinones of the type disclosed in U.S. Pat. No. 3,723,432 is described in U.S. Pat. No. 3,845,128 and is believed to provide a substantial improvement over prior procedures. However, this process nevertheless still relies upon the use of alkyl halides which are relatively expensive and also tends to involve rather lengthy reactive times.

The principal object of the present invention is to provide a new and more effeicient process for the preparation of 2-alkylaminophenyl ketones.

Briefly stated, the present invention involves the preparation of 2-substituted aminophenyl ketones by reacting a corresponding 2-aminophenyl ketone, an aldehyde or ketone, a borohydride and strong acid. The reaction provides particularly high yields and is surprisingly efficient, especially in view of the known ability of the borohydrides to reduce phenyl ketones to their corresponding benzhydrols.

More particularly, the process of the present invention involves the preparation of 2-substituted aminophenyl ketones of the formula I:

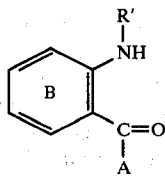

wherein R' is sec.-alkyl of 3 to 7 carbon atoms, cycloalkyl of 5 to 7 carbon atoms, optionally monosubstituted by alkyl of 1 to 4 carbon atoms, optionally mono- or di-substituted benzyl or optionally monosubstituted furylmethyl, Ring B is optionally mono- or di-substituted or substituted by alkylenedioxy of 1 or 2 carbon atoms, and A is optionally mono- or di-substituted monocyclic aryl or naphthyl; by reacting together a borohydride, strong acid, a corresponding 2-aminophenyl ketone of the formula II:

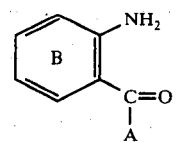

wherein A and B are as above defined, and a compound of the formula III:

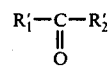

wherein either (1) $R_1'$ and $R_2'$ are each alkyl of 1 to 5 carbon atoms with the proviso that $R_1'$ and $R_2'$ do not exceed 6 carbon atoms; (2) $R_2'$ is hydrogen and $R_1'$ is optionally mono- or di-substituted phenyl or optionally monosubstituted furyl, or (3) $R_1'$ and $R_2'$ together form an alkylene bridge of 4 to 6 carbon atoms optionally monosubstituted by alkyl of 1 to 4 carbon atoms.

The strong acids employed in the invention may, for purposes of definition, be defined as those acids having at least a strength of pH 2 in a 10% by weight aqueous solution, preferably a pH between 0.5 to 1.5 in such solution, and more preferably a pH of about 1.0. Such acids generally include those in the well known category of mineral acids including, by way of illustration only, sulfuric acid, hydrochloric acid, hydrobromic acid, phosphoric acid, nirtric acid and the like. Also included are the acids which may be identified as oganic derivatives of the mineral acids such as methanesulfonic acid, ethanesulfonic acid and p-toluenesulfonic acid. Other strong acids which may be employed include trifluoroacetic acid. The generally preferred acids are sulfuric acid, hydrochloric acid, hydrobromic acid, phosphoric acid and methanesulfonic acid, more preferably sulfuric acid. In general, the particular acid selected may vary depending upon individual preferences and need only be substantially inert, directly or indirectly, with respect to the compounds I and II, viz., does not substantially react or cause a reaction with these compounds leading to a product other than the desired compound I. While certain carboxylic acids, e.g., trifluormethylacetic acid, fall within the definition of the acids employed in the present invention, and perform satisfactorily therein with every indication of being essentially equilvalent to other types of strong acids, it has been observed that trace or small quantities of an alkylated by-product corresponding to the acid tend to be produced. While by-product formation is not deemed substantial and is controllable, it is, accordingly, generally preferred to employ acids which are devoid of carboxylic acid groups, particularly those containing more than one carboxylic acid group, e.g., oxalic acid. In all other cases the many strong acids which we evaluate gave noevidence of undesired side reactions.

The borohydrides employed in the invention are those well known as reducing agents, i.e., the reducing borohydrides. The particularly suitable borohydrides are the alkali metal borohydrides in which the alkali metal is the only metal, particularly the borotetrahydrides such as lithium borohydride, sodium borohydride, and potassium borohydride, more preferably sodium borohydride. Other alkali metal reducing borohydrides include sodium cyanoborohydride.

Many of the reaction conditions and parameters, and/or their relationship to each other, are deemed critical or important in successfully carrying out the process of the present invention, as will be hereinafter disclosed and discussed.

The process of the present invention may be carried out at temperatures in the range of from 0° C to plus 35° C., preferably 10° C to 30° C., and more preferably at temperatures of from 15° C to 28° C. Below about 0° C. solution and other difficulties may be encountered. The upper temperature limit of 35° C. is critical in order to avoid substantial hydrol formation which is detected at about 30° C. and which rapidly increases above 35° C.

The amount of borohydride employed in the reaction may be expressed relative to the amount of the compound II. In general, satisfactory results are obtainable when the mol ratio of borohydride to the compound II is at least 1.7:1. Preferably, the mol ratio of borohydride to the compound II is in the range of from 2:1 to 6:1, more preferably in the range of from 2:1 to 4:1 and desirably in the range of from 2:1 to 3:1. The upper limit on the amount of borohydride is essentially determined by the amount of strong acid employed as will be hereinafter understood. In general, however, mol ratios of borohydride to the compound II in excess of 8:1 are unnecessary and tend toward creating the more difficult operation conditions. The borohydride is preferably employed in finely divided form, e.g., as a powder.

The strong acid employed in the process of the invention reacts with the borohydride as indicated by the liberation of hydrogen during the reaction. The result of this reaction is assumed to be a boron-containing substance which is believed to participate in reduction(s) leading to the desired product. Each acid hydrogen, i.e., hydrogen ion, contained by the strong acid is effective in carrying out the necessary reaction with one mol of borohydride. In terms of this capacity and relationship, the amount of strong acid employed may be appropriately expressed in terms of hydrogen ion equivalents, i.e., the number of mols of hydrogen ion present in the acid. Accordingly, the amount of acid relative to other reactants such as the borohydride and compound II may be expressed in terms of a mol equivalent ratio, i.e., the number of mols of hydrogen ion contained in the acid relative to the absolute or actual number of mols of borohydride or compound II. Our work indicates a theoretical mol equivalent ratio of acid to borohydride of at least 1:1, or more particularly, an amount equivalent on a hydrogen ion basis to the number of mols of borohydride. However, it has been found to be essential to employ an excess of acid relative to the borohydride on a mol equivalent basis in order to avoid formation of substantial amounts of undesired hydrol by-product. Hence, an excess of acid is employed prior to substantial completion of the reaction. The amount of the excess may be small and may be fundamentally defined as the amount necessary to maintain the reaction system sufficiently acidic that it will have acid strength of at least about pH 2, preferably a pH between 0.5 to 1.5, more preferably about pH 1.0. In terms of mols of hydrogen ions, an excess relative to the borohydride of 0.5 percent or even less may be used. Preferably, a mol equivalent excess of acid over borohydride in the range of from 1.0% to 50%, more preferably from 1.5% to 25%, is employed.

One mol of the compound III per mol of the compound II represents the theoretical or stoichometric amount of the compound III for the reaction. To the extent the mechanism and theory of our reaction is at all understood by us, it is possible that the reaction may be carried out employing the compound III in excess as the sole solvent and/or in the presence of a variety of organic solvents includng a solvent of a relatively strong polar type, i.e., in the presence of such organic solvents and a stoichiometric amount of the compound III. In at least a practical sense, however, the process is carried out in a solution in which the solvent is multi-component and comprises at least a small amount of water and at least a small molar excess of at least 20% of the compound III over the stoichiometric amount. Excess amounts of the compound III have a beneficial influence on the reaction and provide the most convenient way of achieving the required and desired operating conditions. For these reasons the total amount of the compound III is desirably an amount represented by a mol ratio of the compound III to the compound II of at least 3:1. The mol ratio of total compound III to compound II is more suitably at least 4:1 and preferably at least 8:1, more preferably from 15:1 to 50:1 and most usually from 20:1 to 45:1. The upper limit on the amount of the compound III is not critical and is more controlled by the limitations of space and other practicalities. Mol ratios in excess of 70:1 offer no respect of additional advantages and are generally avoided. As previously indicated, other organic solvents which are desirably water-miscible and inert in the sense of not having a deleterious effect on the reaction may be added, if desired, although no particular additional benefits are forseen by reason of such addition. Such additional solvents include the common ethers and the like, such as dioxane an tetrahydrofuran. Isopropanol has also been found to be suitable. Besides the inclusion of additional solvents, the reaction mixture may contain other agents which do not have a deleterious effect on the reaction, although the reaction system preferably consists of the compounds II and III, the strong acid, water and the borohydride. The inclusion of substantial amounts of agents having a buffering effect is, however, avoided since the reaction system desirably has an acid pH of at least about 2, preferably between 0.5 and 1.5. The quantities of the various solvents employed in the multi-component solvent, preferably co-solvent, system are indicated to be limited by the requirement that the compound II be essentially fully dissolved, viz. that a substantially homogeneous solution of the compound II in the solvent system be formed. The inability to substantially dissolve the compound II when, for example, excessive water is present, surprisingly results in increased hydrol formation. Thus, the amounts of the various solvents including excess compound III are conrolled by the ability to provide a reaction mixture in which the compound II is substantially dissolved in a homogeneous solutions with the solvent. For definition purposes, we have separately identified and defined the compound III which represents the stoichiometric amount for the reaction and the amount of the same compound which is in excess for solvent and other beneficial purposes. It will be, of course, evident the amounts included in the stoichiometric amount will serve as part of the solvent system until consumed in the reaction even though not treated as a solvent in accordance with the basic definition.

The upper limit on the amount of strong acid and the limits on the amounts of other components of the reaction system including the compound III, water and other optional solvents are interwoven in a somewhat complex manner which may not be subject to exact explanation but which can be, in our view, adequately expressed in different forms, both generally and with regard to the more preferred modes of operation. As indicated, it is fundamentally required that the reaction take place with the compound II substantially in solution with the other liquid components of the reaction system since the failure to do so will sharply reduce yields with the surprising result of correspondingly increased formation of undesired hydrol by-product. Once this condition is recobnized, there is, in one manner of speaking, a relationship between the concentration of the compound III, acid, water and optional solvents that indicates the need to have a certain portion or dilution of the acid relative to these solvents in order to substantially initite the reaction. We find it difficult, however, to assign the reason for failure in certain situations to a single common phenomomen. For example, when the amount of water itself is insufficient, the deficiency may be readily made up by decreasing the amount of the compound III and/or by adding another solvent which is preferably of a polar nature but which is otherwise inert in the reaction in the sense of not adversely affecting the reaction or leading to undesired by-product formation. On the other hand, systems containing the compound III and water in amounts otherwise very satisfactory can be rendered increasingly non-reactive upon the addition of increasing amounts of the strong acid with poor results being realized with total amounts of acid that may constitute only moderate excesses. In the latter case, there is an apparent indication of the formation of complex substance(s) which cause a reduction in yields and eventually an essential cessation of the desired reaction. While we do not wish to be bound by even our own general view as to the nature of such complex or complexes, it is believed that the same are of the nature of salts, probably of the acid addition salt type. Such complexes and/or salts are also indicated to be formed by both the compound II and the desired product of the formula I. Hence, it has been observed that a certain amount of acid will cause an apparent reduction in yield but that a good portion of the apparent yield loss can be recovered in the form of the desired product by allowing the reaction mixture to stand for a period of time and/or by treating with a strong base such as sodium hydroxide or an anhydrous tertiary amine in accordance with standard and well known procedures for recovering a free base acid addition salt form. Hence, the present invention contemplates in its less preferred embodiments producing the compound I in free base and acid addition salt forms and liberating the acid from the salt form to recover additional compound I in free base form. When the amount of acid resulting in good yields of compound I in free base form along with recoverable quantities of the compound in acid addition salt form is increased, the reaction producing the compound I in any form rapidly reaches the point of substantial cessation and markdly reduced yields. It is the apparent complexes formed with the compound II and resulting in a substantial cessation of the reaction that are of less certainty as to identification, and the fact that further dilution of the latter system with water may result in a resumption of the desired reaction sheds little light on the subject but does confirm the basic interrelationship of the solvents, particularly water, and the amount of acid in the reaction. Hence, the amounts of acid and the individual solvent components, i.e., the amounts of the compound III, water and any optional solvents, can be expressed as determined by the requirements that the same are each in an actual amount and proportioned to each other so that the reaction within the aforesaid temperature is substantially initiated, e.g., result in a total yield of compound I of at least 50% including any product in acid addition salt form, while at the same time such amounts and proportions are such as to satisfy the previously mentioned requirement that the compound II be maintained substantially in solution. More simply stated, such amounts and proportions are such as to substantially initiate reaction within said temperature range in a homogeneous solution.

The reaction inhibiting complexes may possibly also explain at least in part the inability of the reaction to substantially proceed in he water deficient system first mentioned above. On the other hand, other considerations involving the dielectrics and ionization capacity of the system are apparently indicated to be influential, if not controlling, in such system. While, as indicated, the system deficient in water may be rectified solely by the addition of organic solvents such as excess compound III, it is indicated that water has the greater influence in rectifying a deficient system and such influence is consistent with the fact that water is the more potent of the practical ionizing solvents. Hence, it can be further indicated that a certain minimum amount of water will have the desired effect of initiating the reaction, so long as the amount of water necessary does not result in substantial dissolution of the compound II. On the other hand, it is also indicated that essentially only substantial excesses of acid will create non-reactive conditions which may not be rectified by adding water without resulting in separation of the compound II from solution or truly impractical conditions. Hence, in another manner of expressing the required conditions for reaction, the minimum amount of water is at least sufficient to substantially initiate the reaction, e.g., result in at least a 50% yield of the compound I after taking into account any product in salf form, while the uper limit on the amount of acid is that amount which, if increased, would cause a substantial cessation of the reaction, e.g., a reduction in yield to below said 50% yield, the requirements as to temperature, solution and minimum amounts of the compound III, acid and borohydride being as previously stated.

It is evident from the foregoing that the amounts of acid and water in the reaction bear a non-exclusive relationship to each other and that each may vary over a fairly wide range. However, the more suitable amounts of water may be expressed relative to the acid, and vice versa, on the basis of the total water in the reaction being equivalent to the amount provided by introducing the strong acid employed in the form of an aqueous solution having a concentration of from 10% to 90% by weight, preferably 15% to 70%, and more preferably 25% to 60%.

The further indication that the amount of any given acid that will cause a cessation of the reaction under any given set of conditions will vary depending under certain factors relating to its strength and, more particularly, its ionization capability, increases the difficulty of stating a numerical upper limit on the amount of acid that would be scientifically applicable to all strong acids. However, an actual mol ratio of acid to the compound II in excess of about 12:1 represents a practical upper limit and is indicated as not to be exceeded without increasing those difficulties associated with undesired complex formation with essentially all the strong acids. It is generally preferred that the actual mol ratio of acid to the compound II does not exceed 5:1, more preferably not in excess of 4:1. In the preferred modes of operation employing the more preferred acid, i.e., sulfuric acid, it is indicated that the actual mol ratio to the compound II will not exceed 5:1 if a substantial cessation of the reaction is to be avoided. Preferably, the actual mol ratio of sulfuric acid to the compound II does not exceed 4:1 in order to avoid the need to chemically liberate significant quantities of the compound I from its acid addition salt form. Desirably, the actual mol ratio of sulfuric acid to the compound II is in the range of from 1:1 to 3:1, more preferably in the range of from 1.15:1 to 2:1.

In general, it is preferred to carry out the reaction by establishing a solution prepared by mixing the compounds II and III and an aqueous solution of the strong acid, and then add the borohydride thereto at a rate desired for control of the reaction. In a less preferred embodiment, the acid and borohydride may be added alternately in small successive additions, provided that the acid present in the reaction system exceeds the amount of borohydride on a mol equivalent basis. Other modes of proceeding will occur to those skilled in the art including the addition of the reactants at a temperature below the reaction temperature followed by a controlled increase in temperature as required to initiate the reaction. The desired product of the formula I in free base or acid addition salt form may be recovered from the reaction mixture by working up by conventional procedures, and the product to the extent in acid addition salf form may be readily converted to the free base by conventional procedures, as previously indicated. Reaction times are generally of the order of from 20 minutes to 10 hours, more usually 30 minutes to 4 hours, and in this respect provides a further advantage over the process described in U.S. Pat. No. 3,845,128. In general, the reaction may be readily carried out to provide good yields of the order of at leadt 50% on a molar basis, and high yields of the order of at least 75%, generally from 85% to about 100%, more usually 90% to 99%, are readily obtainable under preferred operating conditions.

The process of the invention is particularly preferred for the introduction of acyclic branched alkyl groups, i.e., each of $R_1'$ and $R_2'$ are alkyl, and especially for isopropylations.

The compounds of the formulae II and III are each well known or may be prepared from known materials by established procedures.

The following examples are given for purposes of illustration and discussion only, the borohydride in all cases being used in powdered form.

Examples 1–19 as recorded in the following Table I represent trials in which the amount of 4-methyl-2-aminobenzophenone (a compound III in amount of 21.1 grs. or 0.1 mol) is held constant and the amount of other reaction system components including acetone (the compound III), borohydride (sodium borohydride), acid (sulfuric acid) and water are varied. In these examples, the reaction system is maintained at 20°–25° C. throughout the reaction and the rate of addition of the borohydride is controlled accordingly, such addition requiring in most cases about 60 minutes, after which the reaction system is stirred for an additional 60 minutes, followed by filtering. The filtrate is concentrated and the residue dissolved in about 88 mls. of heptane and the resulting solution extracted first with 20 mls. of 4N. ammonium hydroxide solution, then three times each with 10 mls. of 2N. sulfuric acid, and then washed with 10 mls. of 0.5N sulfuric acid. The heptane is distilled off to obtain the desired 2-(N-isopropylamino)-4-methylbenzophenone which boils at 180°–185° C./5 mm Hg.

TABLE I

| Ex. No. | Wt. of acetone | Mols of acetone | Mol ratio acetone/cpd.II | Wt. of $H_2SO_4$ | Wt. of water | Wt. of $NaBH_4$ | Mol Equiv. Ratio acid/borohydride | % yield cpd. I | REMARKS |
| --- | --- | --- | --- | --- | --- | --- | --- | --- | --- |
| 1 | 55 | .95 | 9.5:1 | 14 | 464 | 10.4 | 1.05:1 | 6.5 | Poor solution-benzhydrol |
| 2 | 55 | .95 | 9.5:1 | 14 | 172 | 10.4 | 1.05:1 | 59 | Marginal solution-benzhydrol |
| 3 | 55 | .95 | 9.5:1 | 14 | 86 | 10.4 | 1.05:1 | 96 | Imperfect solution: 4% benzhydrol |
| 4 | 55 | .95 | 9.5:1 | 14 | 43 | 10.4 | 1.05:1 | 79 | Imperfect solution: 20% benzhydrol |
| 5 | 75 | 1.3 | 13:1 | 14 | 43 | 10.4 | 1.05:1 | 80 | Imperfect solution: 5% compound II; 15% benzhydrol |
| 6 | 55 | .95 | 9.5:1 | 14 | 24 | 10.4 | 1.05:1 | 88 | Benzhydrol present: trace comp II |
| 7 | 75 | 1.3 | 13:1 | 14 | 24 | 10.4 | 1.05:1 | 90 | Benzhydrol present: trace comp II |
| 8 | 125 | 2.16 | 21.6:1 | 14 | 24 | 8.0 | 1.36:1 | 94 | Trace Compound II: trace of benzhydrol |
| 9 | 200 | 3.45 | 34.5:1 | 14 | 24 | 10.4 | 1.05:1 | 99 | Compound II: trace of benzhydrol |
| 10 | 25 | .43 | 4.3:1 | 14 | 15 | 10.6 | 1.025:1 | 75 | 25% compound II |
| 11 | 50 | .86 | 8.6:1 | 14 | 15 | 10.6 | 1.025:1 | 86 | Trace compound II: benzhydrol |
| 12 | 56 | .97 | 9.7:1 | 14 | 15 | 10.6 | 1.025:1 | 88 | Trace compound II: benzhydrol |
| 13 | 100 | 1.72 | 17.2:1 | 14 | 15 | 10.6 | 1.025:1 | 90 | 5% compound II: benzhydrol |
| 14 | 190 | 3.28 | 32.8:1 | 14 | 15 | 10.6 | 1.025:1 | 98 | Trace benzhydrol |
| 15 | 17 | .295 | 2.95:1 | 14 | 0.3 | 10.6 | 1.025:1 | 4 | 96% compound II |
| 16 | 55 | .96 | 9.6:1 | 14 | 0.3 | 10.6 | 1.025:1 | 51 | 49% compound II |
| 17 | 200 | 3.45 | 34.5:1 | 14 | 0.3 | 10.6 | 1.025:1 | 90 | 10% compound II |
| 18 | 125 | 2.16 | 21.6:1 | 28 | 24.3 | 8.0 | 2.73:1 | 99 | Trace compound II |
| 19 | 125 | 2.16 | 21.6:1 | 56 | 24.6 | 8.0 | 5.46:1 | 28 | Increased to 38% on basicification |

The foregoing Examples 1 and 2 show the adverse effect of increasing the amount of water to the point where a poor essentially non-homogenous solution in the Example 1 results in a marked reduction in yields. Examples 3–5 are essentially judged to be homogenous but imperfect solutions which give good results with some benzohydrol by-product being produced.

Examples 6 and 7 similarly reflect systems in which the amount of water relative to acetone is high with benzhydrol easily detected as by-product. Examples 8 and 9 show the beneficial effects of increasing the amount of acetone to obtain essentially optimum solutions such that Example 8 is judged to employ the best proportions for a commercial scale operation and Example 9 the best proportions for a laboratory scale reaction. Examples 10–14 generally reflect a series of good to excellent yields of desired product with mixed results in terms of the content of the balance of the reaction mixture.

Example 15 shows that a system containing small amounts of both water and acetone is insufficient to generate the desired reaction and is judged to reflect the inability of the reaction to proceed in a medium which is deficient in dielectric character. Examples 16 and 17 reflect the substantial improvement effected over Example 15 merely by increasing the amount of acetone which is polar and judged to substantially improve the dielectric character of the reaction medium.

Example 18 shows that doubling the amount of sulfuric acid provides good results. However, Example 19 shows that increasing to the amount of sulfuric acid to 4 times the amount employed in Example 8 substantially impedes the reaction with the result that only 28 percent of the desired product in free base form is produced while an additional 10 percent of the desired product is produced in acid addition salt form as indicated by the recovery of the additional 10 percent in free base form on treatment of the reaction mixture with triethyl amine. Such treatment with triethyl amine also revealed that the reaction mixture contained about 55 percent unconverted starting material and about 7 percent of material identified as benzhydrol.

EXAMPLE 20

Preparation of
2-(N-isopropylamino)-4-methylbenzophenone.

To a solution of 63.3 gms. of 2-amino-4-methylbenzophenone in 722 mls. of acetone is added 87 gms. of 49% aqueous sulfuric acid. The mixture is cooled to 20° C. With stirring, and by portionwise addition, 31.2 gms. of sodium borohydride is added to the mixture over a period of 70 minutes. After the addition, the mixture is stirred for an additional 5 hours at 25° C. The suspended solids are filtered and then washed with 300 mls. of acetone. The acetone solutions are combined and concentrated. To the concentrate is added 200 mls. of heptane and 60 mls. of 4N ammonium hydroxide. The liquid layers are separated, then the heptane phase is washed with 20 mls. of water, extracted twice with 20 mls. of 2N sulfuric acid each time, and then washed to neutrality with water. The heptane phase is then dried over magnesiun sulphate, filtered, and concentrated under vacuum to a constant weight of 74.5 gms. or crude yield of 98%, which is shown by analysis to constitute an actual yield of about 95% of the desired 2-(N-isopropylamino)-4-methylbenzophenone.

EXAMPLE 21

The above Example 20 is repeated except that 114 gms. of 28% aqueous hydrochloric acid is substituted for the sulfuric acid and the reaction mixture stirred for only one hour after the addition of borohydride to give a crude yield of 100% and actual yield of about 96% of the desired 2-(N-isopropylamino)-4-methylbenzophenone.

EXAMPLE 22

The above Example 20 is repeated except that an equivalent amount of sulfuric acid is introduced using 36% aqueous sulfuric acid, and similarly excellent results are obtained.

EXAMPLE 23

To a 12 liter capacity flask equipped with stirrer and thermometer and secured in an ice/water beth is added sequentially with stirring, 3.9 liters of acetone, 528.3 grams of 2-amino-4-methylbenzophenone, 462 mls. of water and 263 grams of 98% sulfuric acid while controlling the temperature at 20° C. There is then added with stirring 200 grams of sodium borohydride at a rate of 72 grams per hour while controlling the temperature of the resulting reaction mixture at 20°–25° C. Following addition of the borohydride the reaction mixture is stirred at 20°–25° C. for 4 hours followed by filtering off the precipitated solids which are washed with 1.5 liters of acetone. The filtrate and acetone washings are combined and acetone evaporated in vacuo. The heavy orange colored liquid residue is treated with 2 liters of heptane an 350 mls. of 4N ammonium hydroxide and stirred thoroughly until the resulting solids are dissolved. The aqueous phase is separated and the organic phase washed three times each with 125 mls. of 2N. sulfuric acid and then washed with 120 mls. of 0.5 N. ammonium hydroxide. The organic phase is then distilled under vacuum at 80° C. to a constant weight of 594 grams of 2-(N-isopropylamino)-4-methylbenzophenone, b.p. 180°–185° C./5 mm Hg., yield 94%.

EXAMPLE 24

Example 22 is repeated except that in each repetition the sulfuric acid is replaced by a hydrogen ion equivalent amount of: (a) methanesulfonic acid; (b) nitric acid; (c) hydrobromic acid; (d) trifluoroacetic acid; and (e) picric acid, to obtain the desired product in high yields of the order of at least 70%. In the preparation employing trifluoroacetic acid, there is no indication by gas chromatography of the presence of a dialkylated by-product, but a trace indication of a 2-(trifluoroethylamino)-4-methylbenzophenone by-product. If the experiment is repeated with increased acid concentration (less water), the amount of the undesired by-product increases. For these reasons, the generally preferred strong acids are those which are devoid of carboxylic acid groups.

EXAMPLE 25

To a mixture of 21.1 g. of 2-amino-4-methylbenzophenone, 58.4 g. of benzaldehyde and 35 ml. of isopropanol is added dropwise 5.5 ml. of 46% sulfuric acid while maintaining at temperature of 20°–25° C. There is then slowly added 2.7 g. of sodium borohydride while maintaining 20°–25° C. Thereafter three additional separate and alternate additions of 5.5 mls. of 46% sulfuric acid and 2.7 g. of sodium borohydride are effected while maintaining 20°–25° C. and controlling the foaming caused by the borohydride additions. After stirring for 6 hours there is added with cooling 58 g. of sodium bisulfite in 200 ml. of water followed by the addition of 100 ml. of toluene and stirring for 1.5 hours. The toluene layer is separated, washed twice with water and distilled to remove toluene and benzaldehyde. The cooled residue is treated with heptane which is flashed off and the residue cooled to obtain crystals of 2-benzylamino-4-methylbenzophenone.

EXAMPLE 26

Example 25 is repeated except that a molar equivalent amount of furfural is substituted for the acetone to obtain on column chromotography a high yield of 2-(furfurylamino)-4-methylbenzophenone.

EXAMPLE 27

Following the procedure of Example 22 and substituting the appropriate starting material in molar equivalent amounts there is obtained:
a. 2-(N-isopropylamino)-5-chlorobenzophenone;
b. 2-(N-isopropylamino)-4,5-methylenedioxybenzophenone; and
c. 2-(N-isopropylamino)phenyl-2-thienyl ketone.

When A is monocyclic aryl it is preferably phenyl, 2-thienyl, 3-thienyl, 2-furyl or 3-furyl. When A is naphthyl it may be 1-naphthyl or 2-naphthyl. When A is phenyl or naphthyl it is preferably unsubstituted, monosubstituted or disubstituted. When A is thienyl or furyl it is preferably unsubstituted or monosubstituted. Hence, the preferred significances of A may be represented by the group of the formula IV – IX:

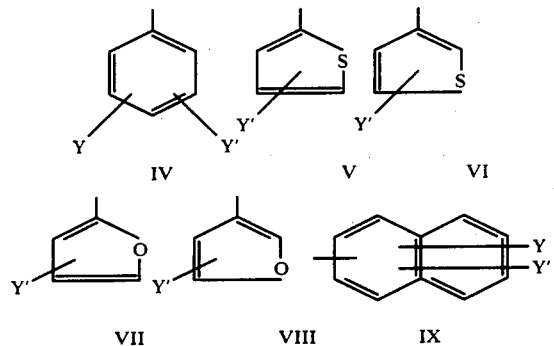

wherein Y is hydrogen, halo of atomic weight of from 18 to 80, i.e., fluoro, chloro or bromo, alkyl of 1 to 4 carbon atoms, alkoxy of 1 to 4 carbon atoms, nitro or trifluoromethyl, and Y' is hydrogen, halo of atomic weight of from 18 to 80, i.e., fluoro, chloro or bromo, alkyl of 1 to 4 carbon atoms or alkoxy of 1 to 4 carbon atoms. A is more preferably phenyl, Y-substituted phenyl, 2-thienyl or Y'-substituted 2-thienyl, and most preferably phenyl or Y-substituted phenyl, particularly phenyl or 4-fluorophenyl.

When the Ring B is substituted, the substituents are preferably one or two of the group consisting of fluoro, chloro, bromo, alkyl of 1 to 4 carbons and alkoxy of 1 to 4 carbon atoms, one of the group consisting of trifluoromethyl, alkylthio of 1 to 4 carbon atoms, nitro and cyano, or an alkylenedioxy of 1 or 2 carbon atoms, such alkylenedioxy preferably being at the 4,5-positions, more preferably 4,5-methylenedioxy.

When R' is mono- or di-substituted benzyl, the substituents are preferably fluoro, chloro, bromo, alkyl of 1 to 4 carbon atoms, alkoxy of 1 to 4 carbon atoms, alkoxy of 1 to 4 carbon atoms, nitro or triofluoromethyl. When R' is monosubstituted furylmethyl, the substituents are preferably fuoro, cloro, bromo or alkyl of 1 to 4 carbon atoms.

Whatever the nature of the group A or substituents on any optionally substituted ring member of the compound II, the present invention is directed to and only contemplates the production of compounds I corresponding to the starting material of the formula II, i.e., the compound II is substantially inert under the reaction conditions in all respects other than 2-amino group where the desired substitution takes place. The optional substituents on the compound II specifically identified herein are deemed merely representative of those providing an otherwise inert compound II as indicated by our investigations in connection with the process of the invention.

When it is stated herein that the 2-unsubstitutedaminophenyl ketone (the compound II) is in solution for reaction purposes, it is to be understood that it is intended to indicate solutions containing the same per se and also solutions of any intermediate product resulting from the combination of the compound II with the other reactants prior to desired product formation. In our works in connection with the process of this invention, there has been found to be essentially no indication of pre-reaction between the compound II and such other required reagents beyond the above-mentioned complexes formed in certain less preferred situations. However, the reaction of the invention is indicated to be somewhat complex mechanistically and it is contemplated that any intermediary products formed prior to the desired product also be substantially dissolved in a homogeneous solution. Hence, it is appropriate to more simply state with regard to the previously indicated requirement for solution conditions that the process of the invention involves a reaction carried out in a substantially homogeneous solution, i.e., the reactants and solvent components together with any intermediate formed prior to the desired product together form a substantially homogeneous solution.

The term "multi-component" as used herein in connection with the solvent or solvent system for the reaction is intended to mean a system or solvent containing two or more individual solvents of which one will be, as indicated, the excess amount of the compound III, and another is water.

While certain preferred embodiments have been disclosed, it will also be evident that various modifications thereof will occur to those skilled in the art without departing from the scope and spirit of the invention.

What is claimed is:

1. The process for producing a 2-monosubstitutedaminophenyl ketone of the formula:

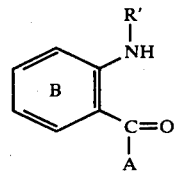

wherein
R' is sec.-alkyl of 3 to 7 carbon atoms, cycloalkyl of 5 to 7 carbon atoms optionally monosubstituted by alkyl of 1 to 4 carbon atoms, optionally mono- or di-substituted benzyl or optionally monosubstituted furylmethyl,
Ring B is optionally mono- or di-substituted or substituted by alkylenedioxy of 1 or 2 carbon atoms, and
A is optionally mono- or di-substituted monocyclic aryl or optionally mono- or di-substituted naphthyl;

from a corresponding 2-unsubstitutedaminophenyl ketone of the formula:

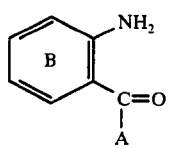

wherein A and B are as above defined, and a carbonyl bearing compound of the formula:

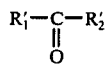

wherein either: (1) $R_1'$ and $R_2'$ are each alkyl of 1 to 5 carbon atoms with the proviso that $R_1'$ and $R_2'$ do not exceed a total of 6 carbon atoms; (2) $R_2'$ is hydrogen and $R_1'$ is optionally mono- or di-substituted phenyl or optionally mono-substituted furyl; and (3) $R_1'$ and $R_2'$ together form an alkylene bridge of 4 to 6 carbon atoms optionally mono-substituted by alkyl of 1 to 4 carbon atoms: comprising reacting at a temperature of from 0° to 35° C.; (A) said 2-unsubstitutedaminophenyl ketone, (B) a strong acid defined by having a strength of at least pH 2.0 in a 10% by weight aqueous solution, (C) a borohydride and (D) a stoichiometric amount of said carbonyl bearing compound, in a multi-component solvent comprising water and at least a 20% molar excess of said carbonyl bearing compound, the mol ratio of borohydride to the unsubstitutedaminophenyl ketone being at least 1.7:1, the mol rato of said acid to borohydride on a hydrogen ion mol equivalent basis being in excess of 1:1 and the individual solvent components and said acid each being in an actual amount and proportioned relative to each other and to said 2-unsubstitutedaminophenyl ketone such as to substantially initiate reaction within said temperature range in a substantially homogeneous solution.

2. The process of claim 1 in which the temperature is from 10° to 30° C. and in which the mol rato of total carbonyl bearing compound to 2-unsubstitutedaminophenyl ketone is at least 3:1.

3. The process of claim 2 in which the mol ratio of borohydride to 2-unsubstitutedaminophenyl ketone is from 2:1 to 6:1, the mol ratio of the carbonyl bearing compound to 2-unsubstitutedaminophenyl ketone is at least 8:1, and the total amount of water present is equivalent to that provided by introducing the acid in the form of an aqueous solution having a concentration of from 10% to 90% by weight.

4. The process of claim 3 in which the temperature is from 15° to 28° C., the mol ratio of borohydride to 2-unsubstitutedaminophenyl ketone is from 2:1 to 4:1, the mol ratio of the total carbonyl bearing compound to 2-unsubstitutedaminophenyl ketone is from 15:1 to 50:1 and the mol equivalent excess of acid over borohydride is in the range of from 1.0% to 50%.

5. The process of claim 4 in which the acid is sulfuric acid, the mol equivalent excess of acid over borohydride is in the range of from 1.5% to 25%, the mol ratio of the total carbonyl bearing compound to the 2-unsubstitutedaminophenyl ketone is from 20:1 to 45:1 and the total amount of water present is equivalent to that provided by introducing the sulfuric acid in the form of a solution having a concentration of from 25% to 60% by weight.

6. The process of claim 1 in which the carbonyl bearing compound is acetone.

7. The process of claim 1 in which A is selected from the group consisting of:

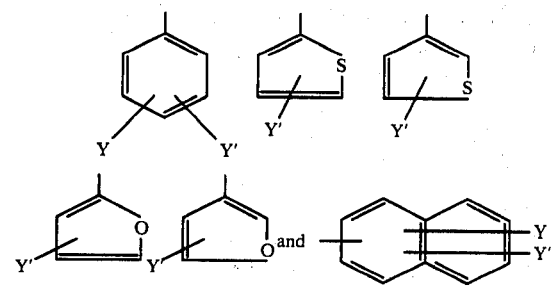

wherein Y is hydrogen, fluoro, chloro, bromo, alkyl of 1 to 4 carbon atoms, alkoxy of 1 to 4 carbon atoms, nitro or trifluoromethyl, and Y' is hydrogen, fluoro, chloro, bromo, alkyl of 1 to 4 carbon atoms or alkoxy of 1 to 4 carbon atoms, and in which Ring B is unsubstituted or mono- or di-substituted by fluoro, chloro, bromo, alkyl of 1 to 4 carbon atoms or alkoxy of 1 to 4 carbon atoms, monosubstituted by trifluoromethyl, alkylthio of 1 to 4 carbon atoms, nitro or cyano or substituted by alkylenedioxy of 1 or 2 carbon atoms.

8. The process of claim 7 in which A is phenyl, Y-substituted phenyl, 2-thienyl or Y'-substituted 2-thienyl.

9. The process of claim 8 in which A is phenyl or Y-substituted phenyl and the carbonyl bearing compound is acetone.

10. The process of claim 9 in which the temperature is from 10° to 30° C. and the mol ratio of total acetone to such 2-unsubstitutedaminobenzophenone is at least 3:1.

11. The process of claim 10 in which the mol ratio of borohydride to 2-unsubstitutedaminobenzophenone is from 2:1 to 6:1, the mol ratio of total acetone to 2-unsubstitutedaminobenzophenone is at least 8:1, and the total amount of water present is equivalent to that provided by introducing the acid in the form of an aqueous solution having a concentration of from 10% to 90% by weight.

12. The process of claim 11 in which the temperature is from 15° to 28° C., the mol ratio of borohydride to 2-unsubstitutedaminobenzophenone is from 2:1 to 4:1, the mol ratio of total acetone to 2-unsubstitutedaminobenzophenone is from 15:1 to 50:1 and the mol equivalent excess of acid over borohydride is in the range of from 1.0% to 50%.

13. The process of claim 12 in which the acid is sulfuric acid, the mol equivalent excess of acid over borohydride is in the range of from 1.5% to 25%, the mol ratio of the acetone to the 2-unsubstitutedaminobenzophenone is from 20:1 to 45:1 and the total amount of water present is equivalent to that provided by introducing the sulfuric acid in the form of a solution having a concentration of from 25% to 60% by weight.

14. The process of claim 1 in which the carbonyl bearing compound is an acyclic ketone.

15. The process of claim 7 in which the carbonyl bearing compound is an acyclic ketone.

16. The process of claim 1 in which the carbonyl bearing compound is a cyclic ketone.

17. The process of claim 1 in which the carbonyl bearing compound is an aldehyde.

18. The process of claim 12 in which the acid is selected from the group consisting of sulfuric acid, hydrochloroic acid, hydrobromic acid, phosphoric acid and methanesulfonic acid.

19. The process of claim 1 in which the borohydride is an alkali metal borohydride in which the alkali metal is the only metal.

20. The process of claim 7 in which the borohydride is an alkali metal borohydride in which the alkali metal is the only metal.

21. The process of claim 12 in which the borohydride is sodium borohydride.

22. The process of claim 20 in which the acid is sulfuric acid.

23. The process of claim 20 in which the acid is hydrochloric acid.

* * * * *